United States Patent
Sakuma et al.

(10) Patent No.: US 10,184,865 B2
(45) Date of Patent: Jan. 22, 2019

(54) VISCOSITY COEFFICIENT CALCULATION DEVICE, INDENTATION TEST DEVICE, TENSILE TESTING DEVICE, VISCOSITY COEFFICIENT CALCULATION METHOD AND PROGRAM

(71) Applicant: National University Corporation Tokyo University of Agriculture and Technology, Tokyo (JP)

(72) Inventors: Atsushi Sakuma, Fuchu (JP); Yuma Sango, Fuchu (JP)

(73) Assignee: NATIONAL UNIVERSITY CORPORATION TOKYO UN, Tokyo (JP)

( * ) Notice: Subject to any disclaimer, the term of this patent is extended or adjusted under 35 U.S.C. 154(b) by 331 days.

(21) Appl. No.: 15/030,597

(22) PCT Filed: Oct. 3, 2014

(86) PCT No.: PCT/JP2014/005055
§ 371 (c)(1),
(2) Date: Apr. 20, 2016

(87) PCT Pub. No.: WO2015/059878
PCT Pub. Date: Apr. 30, 2015

(65) Prior Publication Data
US 2016/0274012 A1  Sep. 22, 2016

(30) Foreign Application Priority Data
Oct. 22, 2013 (JP) .................... 2013-219419

(51) Int. Cl.
*G01L 1/00* (2006.01)
*G01L 3/00* (2006.01)
(Continued)

(52) U.S. Cl.
CPC .............. *G01N 3/08* (2013.01); *G01N 3/42* (2013.01); *G01N 11/10* (2013.01); *G01N 2203/0094* (2013.01)

(58) Field of Classification Search
CPC . G01N 3/08; G01N 3/42; G01N 11/10; G01N 9/00; G01N 2203/0094
See application file for complete search history.

(56) References Cited

U.S. PATENT DOCUMENTS

| | | | |
|---|---|---|---|
| 2010/0160778 A1* | 6/2010 | Eskandari | A61B 8/00 600/438 |
| 2012/0155243 A1* | 6/2012 | Yokoyama | F16F 7/1011 369/247.1 |

(Continued)

FOREIGN PATENT DOCUMENTS

JP  2011-137667 A  7/2011

OTHER PUBLICATIONS

International Search Report for International Application No. PCT/JP2014/005055, issued by the Japan Patent Office dated Nov. 25, 2014.

*Primary Examiner* — Toan K Le

(57) ABSTRACT

A viscosity coefficient calculation device includes a resistivity acquiring part that acquires, for each plurality of periods of time until a specific strains is generated when a load is applied to a sample, a value of deformation resistivity corresponding to an apparent modulus of elasticity when modulus of elasticity considered to be in accordance with Hook's law, and an output part that outputs a value of a viscosity coefficient of the sample from the value of the deformation resistivity for the each plurality of periods of time acquired by the resistivity acquiring part using a relational expression associating the deformation resistivity with the viscosity coefficient, the relational expression being a fractional function for periods of time, the relational (Continued)

expression analytically obtained by substituting the deformation resistivity into a first order differential equation for a stress and a strain obtained from a configuration expression of a viscoelasticity model.

9 Claims, 12 Drawing Sheets

(51) Int. Cl.
*G01L 5/00* (2006.01)
*G01N 3/08* (2006.01)
*G01N 3/42* (2006.01)
*G01N 11/10* (2006.01)

(56) References Cited

U.S. PATENT DOCUMENTS

| 2012/0291528 A1* | 11/2012 | Kuroda | G01N 11/16 73/54.41 |
| 2013/0301411 A1* | 11/2013 | Yoshida | H04W 24/08 370/231 |
| 2014/0020476 A1* | 1/2014 | Inoue | G01N 3/08 73/790 |
| 2014/0221833 A1* | 8/2014 | Oikawa | A61B 8/485 600/438 |
| 2015/0094964 A1* | 4/2015 | Kuroda | G01N 3/08 702/54 |

* cited by examiner

VISCOSITY COEFFICIENT CALCULATION DEVICE, INDENTATION TEST DEVICE, TENSILE TESTING DEVICE, VISCOSITY COEFFICIENT CALCULATION METHOD AND PROGRAM

The contents of the following Japanese and International patent application are incorporated herein by reference:
2013-219419 filed in JP on Oct. 22, 2013; and
PCT/JP2014/005055 filed on Oct. 3, 2014.

BACKGROUND

1. Technical Field

The present invention relates to a viscosity coefficient calculation device, an indentation test device, a tensile testing device, a viscosity coefficient calculation method and a program.

2. Related Art

Viscoelasticity of a substance is elasticity property and viscosity property that the substance has both. Therefore, for knowing the viscoelasticity property, it is preferable to identify a vertical modulus of elasticity and a viscosity coefficient on the basis of an indentation test and the like. As a method for identifying the vertical modulus of elasticity and the like on the basis of the indentation test and the like, for example, Patent Document 1 is known. In Patent Document 1, a relation between deformation amounts and forces at three indentation rates is measured using a three-element solid model, and based on a comparison of three deformation amounts at each level into which the forces are finely divided, physical property values of two elastic elements and one viscous element of the three-element solid model are identified as nonlinear parameters.

Patent Document 1: Japanese Patent Application Publication No. 2011-137667

SUMMARY

However, a difficult analysis approach, where a complicated sequential operation is performed on measured data to identify the physical property values, is used in the method according to the above-described Patent Document 1. Accordingly, a more convenient and accurate identification of the values of viscosity coefficient of viscoelasticity has been desired.

In a first aspect of the present invention, a viscosity coefficient calculation device comprises a resistivity acquiring part that acquires, for each plurality of periods of time until a specific strain is generated when a load is applied to a sample, a value of deformation resistivity corresponding to an apparent modulus of elasticity when modulus of elasticity considered to be in accordance with Hook's law, and an output part that outputs a value of viscosity coefficient of the sample from the value of the deformation resistivity for the each plurality of periods of time acquired by the resistivity acquiring part using a relational expression associating the deformation resistivity with the viscosity coefficient, which is a fractional function for time and is analytically obtained by substituting the deformation resistivity into a first order differential equation for a stress and a strain obtained from a configuration expression of a viscoelasticity model.

In a second aspect of the present invention, an indentation test device comprises an indentation part that indents an indenter into a sample, a load acquiring part that acquires, when the indenter is indented by the indentation part at rates different from each other, a plurality of loads of the indenter and indentation amounts of the sample relative to the loads corresponding to the multiple rates, a resistivity calculation part that calculates a value of deformation resistivity corresponding to an apparent modulus of elasticity when modulus of elasticity considered to be in accordance with Hook's law for each plurality of periods of time from the plurality of the loads and the indentation amounts acquired by the load acquiring part by an expression on the basis of Hertz's theory of elastic contact, and an output part that outputs a value of the viscosity coefficient of the sample from the value of the deformation resistivity for the each plurality of periods of time calculated by the resistivity calculation part using a relational expression associating the deformation resistivity with a viscosity coefficient, which is a fractional function for time and is analytically obtained by substituting the deformation resistivity into a first order differential equation for a stress and a strain obtained from a configuration expression of a viscoelasticity model.

In a third aspect of the present invention, a tensile testing device comprises a pulling part that pulls a sample, a load acquiring part that acquires, when the sample is pulled by the pulling part at a plurality of rates different from each other, a plurality of tensile loads and tensile amounts of the sample relative to the loads corresponding to the plurality of rates, a resistivity calculation part that calculates a value of deformation resistivity corresponding to an apparent modulus of elasticity when modulus of elasticity considered to be in accordance with Hook's law for each plurality of periods of time from the plurality of the loads and the tensile amounts acquired by the load acquiring part, and an output part that outputs a value of viscosity coefficient of the sample from the value of the deformation resistivity for the each plurality of periods of time calculated by the resistivity calculation part using a relational expression associating the deformation resistivity with the viscosity coefficient, which is a fractional function for time and is analytically obtained by substituting the deformation resistivity into a first order differential equation for a stress and a strain obtained from a configuration expression of a viscoelasticity model.

In a forth aspect of the present invention, a viscosity coefficient calculation method comprises a resistivity acquiring step of acquiring, for each plurality of periods of time until a specific strain is generated when a load is applied to a sample, a value of deformation resistivity corresponding to a modulus of elasticity when modulus of elasticity considered to be in accordance with Hook's law, and an output step of outputting a value of viscosity coefficient of the sample from the value of the deformation resistivity for the each plurality of periods of time acquired by the resistivity acquiring step using a relational expression associating the deformation resistivity with the viscosity coefficient, which is a fractional function for time and is analytically obtained by substituting the deformation resistivity into a first order differential equation for a stress and a strain obtained from a configuration expression of a viscoelasticity model.

In a fifth aspect of the present invention, a program allows a computer to function as a resistivity acquiring part that acquires, for each plurality of periods of time until a specific strain is generated when a load is applied to a sample, a value of deformation resistivity corresponding to an apparent modulus of elasticity when modulus of elasticity considered to be in accordance with Hook's law, and an output part that outputs a value of viscosity coefficient of the sample for the each plurality of periods of time from the value of the deformation resistivity acquired by the resistivity acquiring part using a relational expression associating the deformation resistivity with the viscosity coefficient, which is a fractional function for time and is analytically obtained by substituting the deformation resistivity into a first order differential equation for a stress and a strain obtained from a configuration expression of a viscoelasticity model.

It should be noted that the above-described invention summary does not necessarily describe all features of the present invention. Also, a sub-combination of these features may also be the present invention.

DESCRIPTION OF EXEMPLARY EMBODIMENTS

Hereinafter, the present invention will be described through some embodiments of the invention. The following embodiments do not limit the invention according to the claims, and all the combinations of the features described in the embodiments are not necessarily essential to means provided by aspects of the invention.

In the present embodiment, a value of viscosity coefficient μ of a sample having viscoelasticity is calculated. In this case, a deformation resistivity D is used, which corresponds to an apparent modulus of elasticity when modulus of elasticity considered to being in accordance with Hook's law. Further, a relational expression is used, which associates the deformation resistivity D with the viscosity coefficient μ, and is analytically obtained by substituting the deformation resistivity D into a first order differential equation for a stress and a strain obtained from a configuration expression of a viscoelasticity model. The relational expression is to be a fractional function for periods of time t. First, the relational expression will be described.

Figure 1:
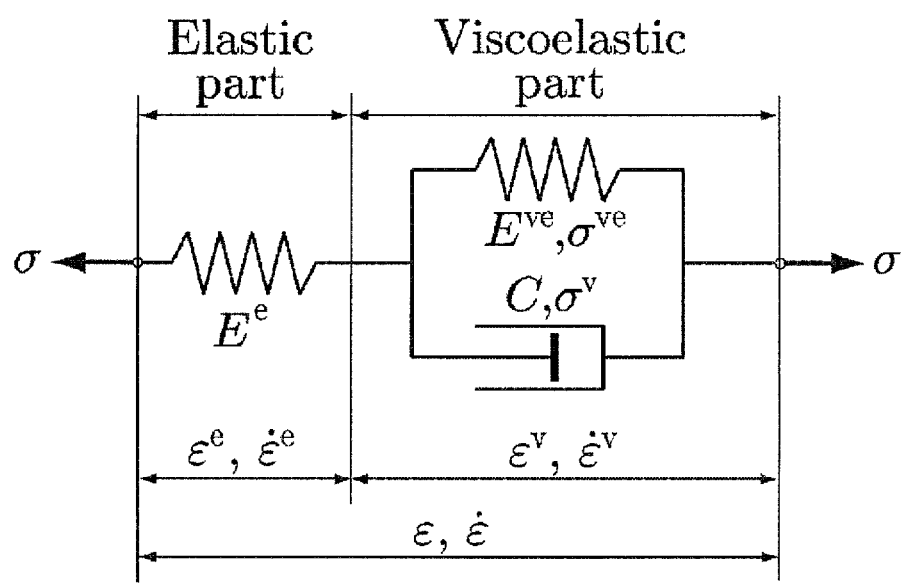
FIG. 1 shows a three-element solid model being one example of a model of a sample having viscoelasticity.

FIG. 1 shows a three-element solid model being one example of a model of a sample having viscoelasticity. With respect to a strain $\varepsilon^e$ and a vertical modulus of elasticity $E^e$ of an elastic part, a vertical modulus of elasticity $E^{ve}$ and a generated stress $\sigma^{ve}$ of a spring element of a viscoelastic part, and a viscosity compliance C, a generated stress $\sigma^v$ and a strain $\varepsilon^v$ of a dash pot element of the viscoelastic part, the relations from the following Expression 1 to Expression 6 are satisfied.

It should be noted that dot over symbol for each physical amount indicates time differentiation, and is substituted by a superscript "·" in the description. Also, line over each physical amount is substituted by a superscript "−" in the description.

$$\varepsilon = \varepsilon^e + \varepsilon^v \qquad \text{EXPRESSION 1}$$

$$\dot{\varepsilon} = \dot{\varepsilon}^e + \dot{\varepsilon}^v \qquad \text{EXPRESSION 2}$$

$$\varepsilon^e = \frac{\sigma}{E^e} \qquad \text{EXPRESSION 3}$$

$$\dot{\varepsilon}^e = \frac{\dot{\sigma}}{E^e} \qquad \text{EXPRESSION 4}$$

$$\sigma = \sigma^{ve} + \sigma^v \qquad \text{EXPRESSION 5}$$

$$\left.\begin{array}{l}\sigma^{ve} = E^{ve}\varepsilon^v \\ \sigma^v = \dfrac{1}{C}\dot{\varepsilon}^v\end{array}\right\} \qquad \text{EXPRESSION 6}$$

Based on the above-described Expressions 1 to 6, a configuration expression for the model is represented as Expression 7.

$$C(E^e + E^{ve})\sigma + \dot{\sigma} = CE^e E^{ve}\varepsilon + E^e\dot{\varepsilon} \qquad \text{EXPRESSION 7}$$

Figure 2:
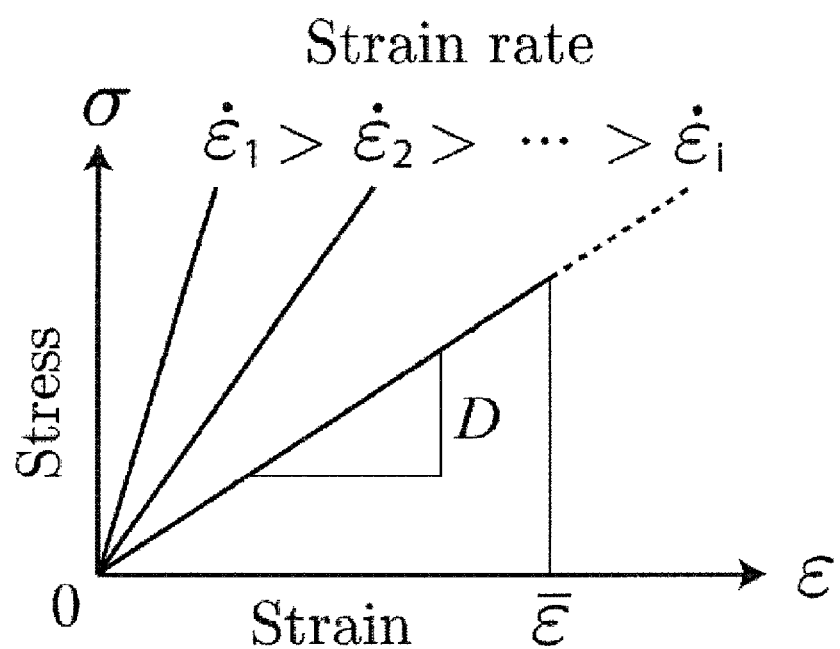
FIG. 2 conceptually shows a stress-strain line diagram relative to a viscoelastic body.

FIG. 2 conceptually shows a stress-strain line diagram relative to a viscoelastic body. When a sample is a viscoelastic body, according to the viscosity that the sample has, the higher the strain rate $\dot{\varepsilon}$, the greater the apparent vertical modulus of elasticity which is the inclination in the drawing. It should be noted that, in FIG. 2, straight lines are drawn for any of the strain rates $\dot{\varepsilon}$ for the sample, which are considered that the stress σ and the strain c are in a linear relation.

Here, a deformation resistivity D is introduced, which corresponds to an apparent modulus of elasticity when the sample is considered to be in accordance with Hook's law. First, as shown in Expression 8, in a period of time t until the strain reaches a specific strain amount ε from a state where the strain is 0, it is assumed for convenience that the strain rate $\dot{\varepsilon}$ is constant during that period. Similarly, it is assumed for convenience that the stress rate $\dot{\sigma}$ is constant during that period until the stress reaches σ from 0.

$$\sigma = \dot{\sigma}t, \; \varepsilon = \dot{\varepsilon}t \qquad \text{EXPRESSION 8}$$

Furthermore, the strain amount ε and the stress σ are considered to be in a linear relation as shown in FIG. 2; in that case, a deformation resistivity D [k Pa] is defined by the following Expression 9. In other words, the deformation resistivity D corresponds to the apparent modulus of elasticity when the strain amount ε and the stress σ of the viscoelastic body are considered to be in accordance with Hook's law. The reason being "the apparent modulus of elasticity" is because an effect of viscosity is included in the deformation resistivity D.

$$D = \frac{\partial \sigma}{\partial \varepsilon} = \frac{\partial \sigma}{\partial t}\frac{\partial t}{\partial \varepsilon} = \dot{\sigma}\frac{1}{\dot{\varepsilon}} = \frac{\sigma}{\varepsilon} \qquad \text{EXPRESSION 9}$$

The inventors of the present invention found that the deformation resistivity D can be analytically obtained as a fractional function for periods of time t calculated from a first order differential equation for the stress and the strain by substituting the deformation resistivity D defined by Expression 9 into the above-described Expression 7 being the configuration expression for the model. That is, the following Expression 10 is obtained by substituting Expression 9 into Expression 7 and simplifying the expression. Expression 10 is a relational expression associating the deformation resistivity D with a viscosity compliance C and the like.

$$D(t) = \frac{CE^e E^{ve} t + E^e}{C(E^e + E^{ve})t + 1} \qquad \text{EXPRESSION 10}$$

According to the above-described Expression 10, given a value set of periods of time t and the deformation resistivity D in that period of time, the viscosity compliance C and the vertical moduluses of elasticity $E^e$ and $E^{ve}$ can be identified as parameters. Since there are three parameters to be identified, it is preferable to have either three value sets or no less than three value sets of the periods of time t and the deformation resistivity D.

Here, the period of time t is a period of time until a specific strain amount ε assumed by Expression 8 is reached, and is obtained as follows. First, in a process of indenting a ball indenter into a soft material such as a viscoelastic body, as recognized from a significant change of the surface shape in the load surface, a phenomenon appears, where a deformation region of the sample significantly changes due to the indentation by the indenter. Here, the deformation caused by the indentation is represented by a superposition of a contact deformation of the indenter which is also generated even in a case of a non-soft material and a compressive deformation of the indenter which is generated in a case of a soft material.

In this case, the contact deformation is shown as Hertz strain $\bar{\varepsilon}_H$ according to Hertz's theory of elastic contact, and the compressive deformation is shown as a rate of change $\bar{\varepsilon}_V$ of the region volume to define the following Expression 11. Expression 11 is intended to show a three-dimensional strain distribution generated in the sample during the indenting process by an equivalent uniaxial strain, and $\bar{\varepsilon}_I$ is called an "equivalent indentation strain".

$$\bar{\varepsilon}_I = \bar{\varepsilon}_H + \bar{\varepsilon}_V \qquad \text{EXPRESSION 11}$$

The Hertz strain $\bar{\varepsilon}_H$ is shown in Expression 12. Note that δ [m] indicates an indentation amount, φ [m] indicates a diameter of the indenter, and ν [–] indicates a Poisson's ratio of the sample.

$$\bar{\varepsilon}_H = -\frac{2}{\pi(1-v^2)}\left(\frac{2\delta}{\phi}\right)^{\frac{1}{2}} \qquad \text{EXPRESSION 12}$$

Also, the rate of change $\bar{\varepsilon}_V$ of the region volume caused by the compressive deformation is shown in Expression 13. Note that h [m] indicates a thickness of the sample.

$$\bar{\varepsilon}_V = -\frac{\delta}{h} - \frac{2}{3}\ln\left\{\frac{2h + 3\left(\frac{\phi}{2}-\delta\right)}{2h + \frac{3}{2}\phi}\right\} \qquad \text{EXPRESSION 13}$$

The period of time t until any equivalent indention strain $\bar{\varepsilon}_I$ is reached is represented by Expression 14 if using an amount of change $\Delta\bar{\varepsilon}_I$ of an equivalent indention strain and a rate $\dot{\bar{\varepsilon}}_I$ of the equivalent indention.

$$t = \frac{\Delta \bar{\varepsilon}_I}{\dot{\bar{\varepsilon}}_I} \qquad \text{EXPRESSION 14}$$

An indentation rate $\dot{\delta}$ [m/s] in the indentation test is represented by Expression 15 using an indentation amount δ.

$$\dot{\delta} = \frac{\partial \delta}{\partial t} \qquad \text{EXPRESSION 15}$$

By substituting Expressions 13 and 15 from Expression 11 into Expression 14 and simplifying the expression, Expression 16 for period of time t is obtained.

$$t = \frac{\Delta \bar{\varepsilon}_I}{\left(\begin{array}{l}-\frac{2}{\pi(1-v^2)}\frac{1}{\phi}\left(\frac{2\delta}{\phi}\right)^{-\frac{1}{2}} - \\ \frac{1}{h} + \frac{2}{2h + 3\left(\frac{\phi}{2}-\delta\right)}\end{array}\right)\dot{\delta}} \qquad \text{EXPRESSION 16}$$

Here, the deformation resistivity D when t→0 is represented as a short-term vertical modulus of elasticity $D_0$, and the deformation resistivity D when t→∞ is represented as a long-term vertical modulus of elasticity $D_\infty$. The short-term vertical modulus of elasticity $D_0$ and the long-term vertical modulus of elasticity $D_\infty$ are obtained from Expression 10, as shown in Expression 17 and Expression 18 respectively.

$$D_0 = E^e \qquad \text{EXPRESSION 17}$$

$$D_\infty = \frac{E^e E^{ve}}{E^e + E^{ve}} \qquad \text{EXPRESSION 18}$$

The long-term vertical modulus of elasticity $D_\infty$ is equivalent to a case when the strain rate $\dot{\varepsilon}$ is infinitesimal. Therefore, the long-term vertical modulus of elasticity $D_\infty$ is a parameter excluding effects caused by the viscosity and, accordingly, is equivalent to Young's modulus E defined by Hook's law.

Next, the relation between the viscosity compliance C and the viscosity coefficient μ in FIG. 1 will be described. The viscosity compliance C [$Pa^{-1} \cdot s^{-1}$] is defined by Expression 19.

$$\dot{\varepsilon} = C\sigma \qquad \text{EXPRESSION 19}$$

With respect to a three-dimensional isotropic viscoelastic body, a strain change $\dot{\varepsilon}^v$ caused by the viscosity is represented by Expression 20 using the viscosity coefficient μ according to a similarity to an expression often used in an isotropic elastic body.

$$\{\dot{\varepsilon}^v\} = \frac{1}{2\mu}\{\sigma'\} \qquad \text{EXPRESSION 20}$$

It should be noted that $\{\sigma'\}$ means a deviation stress and is defined by Expression 21 for an x direction.

$$\sigma'_x = \frac{1}{3}(2\sigma_x - \sigma_y - \sigma_z) \qquad \text{EXPRESSION 21}$$

Here, in a case where it is assumed that the indentation test is a measurement under a uniaxial stress, Expression 22 is obtained by substituting Expression 21 into Expression 20.

$$\dot{\varepsilon}^v_x = \frac{1}{2\mu}\frac{1}{3}2\sigma_x = \frac{1}{3\mu}\sigma_x \qquad \text{EXPRESSION 22}$$

By comparing Expression 22 with Expression 19, the relation between the viscosity compliance C and the viscosity coefficient µ [Pa·s] is obtained, as shown in Expression 23. Therefore, if the value of the viscosity compliance C is identified by Expression 10, the value of the viscosity coefficient µ is also identified.

$$\mu = \frac{1}{3C} \qquad \text{EXPRESSION 23}$$

As above, it was described that the deformation resistivity D is represented by a fractional function for periods of time t, and by using the fractional function, the value of the viscosity coefficient µ is identified as long as the values of the deformation resistivity D and the periods of time t are given. However, since the deformation resistivity D and the periods of time t cannot be directly given in some cases, the relation of the deformation resistivity D and the periods of time t with the indentation amount δ and the indentation load F being physical quantities directly obtained from the indentation test device, will be further described.

Based on Hertz's theory of elastic contact, the indentation amount δ, the indentation load F and the deformation resistivity D have a relation as shown in Expression 24.

$$F = \frac{4}{3}\frac{D}{1-v^2}\left(\frac{\phi}{2}\right)^{\frac{1}{2}}\delta^{\frac{3}{2}} \qquad \text{EXPRESSION 24}$$

Here, for convenience, the amount of change $\Delta\varepsilon_I^-$ of the strain is presumed according to a standard value of a strain amount that may be generated on the sample, and the value of the deformation resistivity D is calculated using Expression 24 from the measured values of the indentation amount δ, the indentation rate $\dot{\delta}$ and the indentation load F directly obtained from the indentation test device, and the period of time t is calculated from Expression 16 as well. Using these deformation resistivity D and periods of time t, the value of the viscosity compliance C is identified by Expression 10, and the value of the viscosity coefficient µ is further identified by Expression 23.

It should be noted that by now, it had not been considered that Expression 7 being a configuration expression for a three-element model can be analytically solved by Expression 9. Since there is a method for solving the expression approximately instead of analytically solving it, the method will be described as a comparative example.

A first comparative example is a method for presuming a solution to be an exponential function for the periods of time t relative to Expression 7, as shown in Expression 25. Expression 25 shows a stress response in a case where a step strain ε=1 (t) is given.

$$\frac{\sigma}{\varepsilon} = \sum_i E_i e^{-\frac{E_i}{\mu_i}t} \qquad \text{EXPRESSION 25}$$

Here, $E_i$ and $\mu_i$ are the modulus of elasticity for each spring element and the viscosity coefficient for the dash pot element respectively. The period of time t is any time. A sheer modulus of elasticity G (t) in any period of time Expression 7 is approximately solved assuming Expression 25. Here, $G_0$ is a short-term linear modulus of elasticity, $G_\infty$ is a long-term linear modulus of elasticity, and β is an attenuation coefficient.

$$G(t) = G_\infty + (G_0 - G_\infty)e^{-\beta t} \qquad \text{EXPRESSION 26}$$

By replacing the vertical modulus of elasticity E with the deformation resistivity D in the relation between the sheer modulus of elasticity G and the vertical modulus of elasticity E relative to Expression 26, Expression 27 is obtained.

$$D(t) = D_\infty + (D_0 - D_\infty)e^{-\beta t} \qquad \text{EXPRESSION 27}$$

In this case, the relation between the attenuation coefficient β and the viscosity coefficient µ is given by Expression 28.

$$\beta = \frac{(E^e)^2}{(E^e + E^{ve})\mu} \qquad \text{EXPRESSION 28}$$

According to the above, in the first comparative example, it is also possible to identify the value of the viscosity coefficient µ from the value of the average resistivity D approximately solving Expression 7. However, since the average resistivity D in Expression 27 for the first comparative example is represented using the exponential function for the periods of time t, the actual calculation by numerics becomes complicated. Furthermore, since the period of time t is any time, the value of the viscosity coefficient µ changes significantly depending on in which period of time t the average resistivity D is used to identify the viscosity coefficient µ.

On the other hand, according to the present embodiment, Expression 10 is a fractional function where a first-order term of the period of time t is included in both the denominator and the numerator. Therefore, the actual calculation by the numerics is also easy, and the effects caused by the time can be approximately offset in the calculation of the value of the viscosity coefficient µ. Also, in the period of time t when identifying the parameters in Expression 10, the value of the viscosity coefficient µ can be identified under a more uniform condition by using Expression 16.

A second comparative example is a method used in the above-described Patent Document 1. As described above, in this method, the relation between the indentation amount δ and the load F at three indentation rates $\dot{\delta}$ is measured corresponding to that there are three parameters to be identified. Furthermore, based on a comparison among the three indentation amounts δ at each level into which the load F is finely divided, the physical property values of two elastic elements and one viscous element of the three-element solid model are identified as nonlinear parameters. In this case, a sequential operation for the measured data is performed.

Therefore, according to the second comparative example, more measured data becomes to be used for the sequential operation; for example, it becomes to use about equal to or more than 100 to 200 of measuring points. Therefore, the testing time for the indentation test and the like are increased. Furthermore, the calculation amounts for the sequential operation also increase and the calculation time increases.

On the other hand, according to the present embodiment, the parameters in Expression 10 are directly identified using the value of the average resistivity D in the period of time t. Therefore, the identification accuracy of the parameters and the value of the viscosity coefficient introduced from the parameters are high. Further, since it is sufficient that the number of the value sets of the periods of time t and the average resistivity D is about the number of the parameters, the time for the test is decreased and the calculation time is also decreased.

Figure 3:
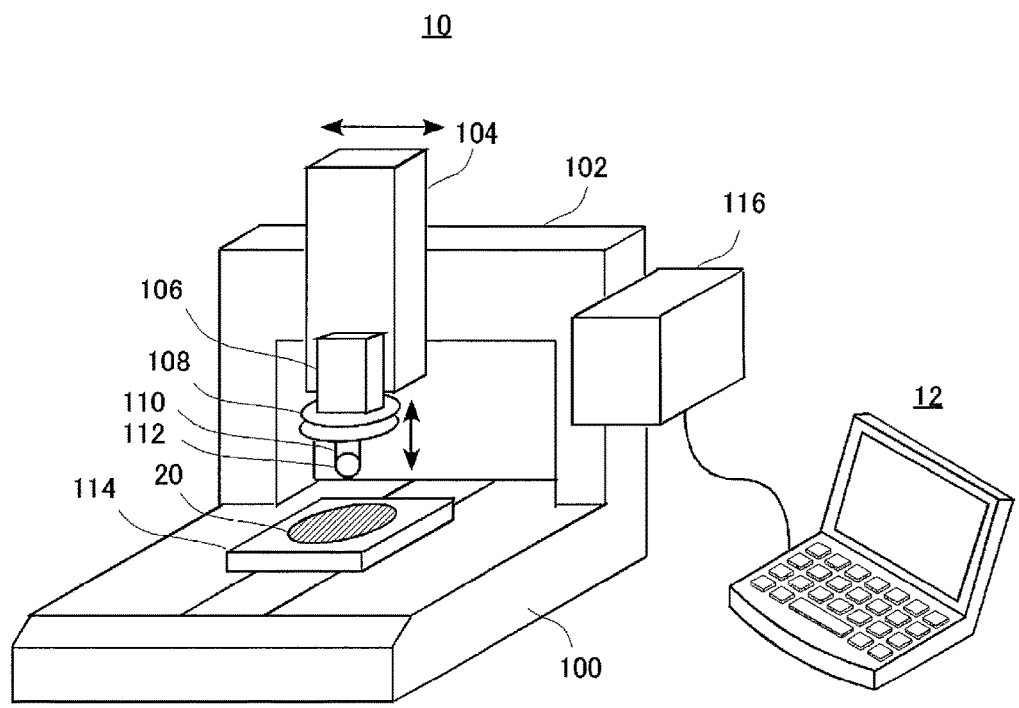
FIG. 3 shows a schematic perspective view of an indentation test system for identifying a viscosity coefficient μ of the sample.

FIG. 3 shows a schematic perspective view of an indentation test system for identifying a value of a viscosity coefficient μ of a sample 20. The indentation test system comprises an indentation test device 10 and a viscosity coefficient calculation device 12 that sends and receives information between itself and the indentation test device 10.

The indentation test device 10 has a base 100, a frame 102 provided on the base 100, and a head 104 supported by the frame 102. A stage 114 is movably arranged on the base 100. The sample 20 is placed on the stage 114.

The head 104 is movable on the frame 102 in a horizontal direction. The head 104 supports an actuator 106, a load cell 108, a load shaft 110, and a ball indenter 112. The actuator 106 moves the load cell 108, the load shaft 110 and the ball indenter 112 integrally in a vertical direction. The load cell 108, the load shaft 110 and the ball indenter 112 are arranged in series in this order.

A control part 116 controls the horizontal movement of the head 104, and controls the vertical movement of the actuator 106 as well. The control part 116 further acquires a position of the ball indenter 112 in the vertical direction and a load F applied to the load cell 108.

In the above-described indentation test device 10, the control part 116 indents the ball indenter 112 into the sample 20 by driving the actuator 106 with an indentation amount δ at the indentation rate $\dot{\delta}$ based on the instruction from the viscosity coefficient calculation device 12 and the like. The control part 116 acquires the load F of the load cell 108 during indenting.

The control part 116 outputs the indentation amount δ, the indentation rate $\dot{\delta}$ and the load F to the viscosity coefficient calculation device 12. In this case, the control part 116 may output the indentation amount δ and the like in real time, and may record the indentation amount δ and the like as logs from the beginning until finishing of indentation and output the indentation amount δ and the like to the viscosity coefficient calculation device 12 after the indentation is finished or when requested from the viscosity coefficient calculation device 12.

Figure 4:
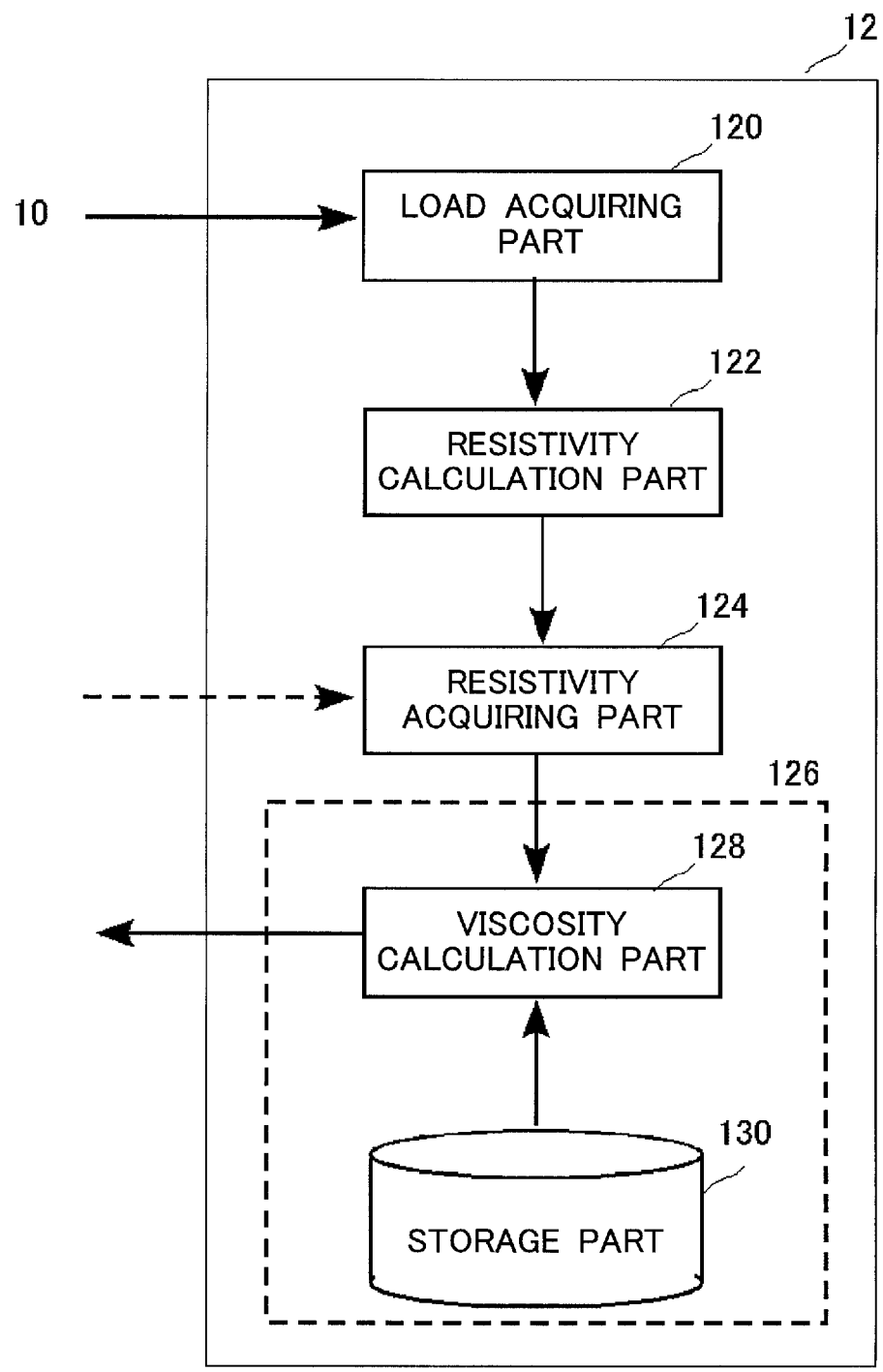
FIG. 4 shows a function block of a viscosity coefficient calculation device 12.

FIG. 4 shows a function block of the viscosity coefficient calculation device 12. One example for the viscosity coefficient calculation device 12 is a personal computer.

The viscosity coefficient calculation device 12 has a load acquiring part 120, a resistivity calculation part 122, a resistivity acquiring part 124 and an output part 126. The output part 126 further has a viscosity calculation part 128 and a storage part 130. Respective functions will be described below. These functions may be realized by installing software programs into a personal computer.

Figure 5:
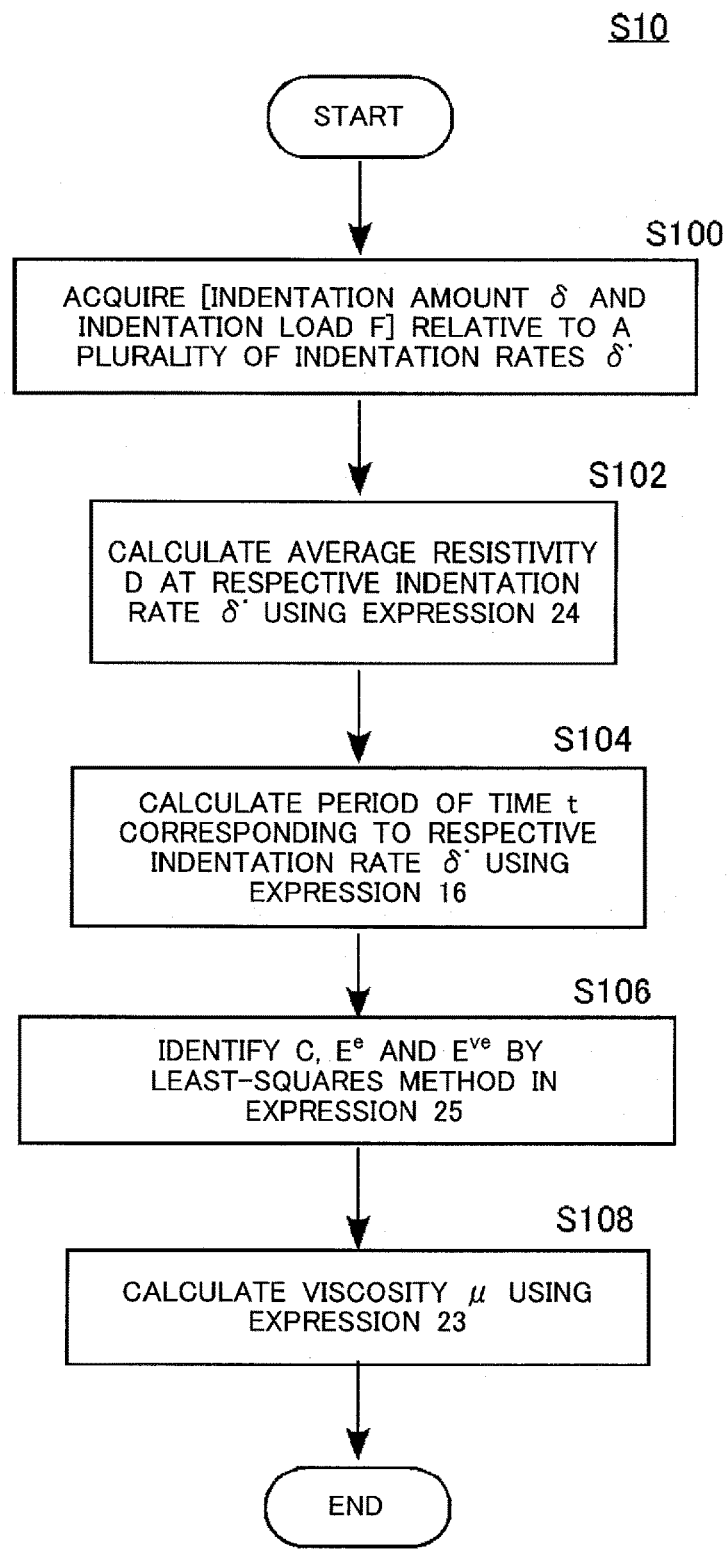
FIG. 5 is a flowchart showing one example of operations of the viscosity coefficient calculation device 12.

FIG. 5 is a flowchart showing one example of an operation S10 of the viscosity coefficient calculation device 12. First, the load acquiring part 120 acquires the load F and the indentation amount δ from the indentation test device 10 corresponding to the indentation rate $\dot{\delta}$ (S100).

In this case, in the indentation test device 10, a test for measuring the load F and the indentation amount δ corresponding to the load F when indenting the ball indenter 112 into the sample 20 at a constant indentation rate $\dot{\delta}$ is performed at a plurality of indentation rates $\dot{\delta}$ different from each other. For example, corresponding to that there are three parameters to identify in Expression 10, the indentation test device 10 performs the test at three indentation rates $\dot{\delta}$, and the load acquiring part 120 acquires load F and the indentation amount δ corresponding to each of the three indentation rates $\dot{\delta}$.

The resistivity calculation part 122 calculates the deformation resistivity D using Expression 24 from the indentation amount δ and the load F which are acquired by the load acquiring part 120 (S102). For example, the deformation resistivity D is calculated by fitting the calculation values of the load F and the indentation amount δ corresponding to the load F in Expression 24 to the measured values of the load F and the indentation amount δ acquired by the load acquiring part 120. In this case, the resistivity calculation part 122 calculates the deformation resistivity D corresponding to each of the plurality of the indentation rates $\dot{\delta}$ acquired by the load acquiring part 120. It is preferable to set the same range of the indentation amounts δ for fitting for each indentation rate $\dot{\delta}$.

The resistivity calculation part 122 further calculates the period of time t using Expression 16 from the indentation rate $\dot{\delta}$, the indentation amount δ and the amount of change $\Delta\varepsilon_I^-$ of the strain which are acquired by the load acquiring part 120 (S104). In this case, the resistivity calculation part 122 calculates the respective periods of time t respectively corresponding to the plurality of the indentation rates $\dot{\delta}$ acquired by the load acquiring part 120. It should be noted that the steps S102 and S104 may be in any order.

The viscosity calculation part 128 identifies the viscosity compliance C and the vertical moduluses of elasticity $E^e$ and $E_{ve}$ in Expression 10 (S106). In this case, the viscosity calculation part 128 specifies the viscosity compliance C and the vertical moduluses of elasticity $E^e$ and $E^{ve}$ using the least-squares method of Expression 29 for a plurality of value sets of the average resistivity D and the period of time t that the resistivity acquiring part 124 acquires from the resistivity calculation part 122 (the same step).

$$f(C, E^e, E^{ve}) = \sum_t \left\{ D(t) - \frac{CE^e E^{ve} t + E^e}{C(E^e + E^{ve})t + 1} \right\}^2 \quad \text{EXPRESSION 29}$$

The viscosity calculation part 128 calculates the viscosity coefficient μ using Expression 23 from the viscosity compliance C specified at the step S106 (S108) and outputs a result to a display, memory and the like of the personal computer. The viscosity calculation part 128 may further calculate the long-term vertical modulus of elasticity $D_\infty$ and the short-term vertical modulus of elasticity $D_0$ using Expression 18 from the vertical moduluses of elasticity $E^e$ and $E^{ve}$ specified at the step S106 and output them. According to the above, the operation S10 is finished.

Each relational expression used in the operation S10, including the above-described Expression 29, is prestored in the storage part 130 and is referred by the viscosity calculation part 128 and the like at each step. Also, the numerics such as the diameter φ of the ball indenter 112 and the like pre-given in the test are also pre-stored in the storage part 130. Alternatively, the pre-given numerics of the diameter φ of the ball indenter 112 and the like may be acquired by the load acquiring part 120 from the indentation test device 10 and the like at the step S100.

FIRST EXAMPLE

As a first example, values of viscosity coefficients μ for a plurality of samples of viscoelastic body were calculated based on the above-described embodiment. As the indentation test device, a desktop type indentation test machine "SoftMeasure HS-3001" of HORIUCHI ELECTRONICS CO., LTD was used. A ball indenter with the diameter of 10 mm, as the diameter φ of the ball indenter, was used.

As the samples, four types of skin model material "BIO-SKIN" of Beaulax Co., Ltd. named LV2, LV4, LV6 and LV8 were used. Each sample was LV2, LV4, LV6 or LV8 in a descending order of durometer hardness. A thickness h of the samples was 15 mm in a central part.

For each sample, measured were loads F and indentation amounts δ corresponding to the loads F when indenting the ball indenter into the central part of the sample at a constant indentation rate $\dot{\delta}$. The test was performed at three rates: 0.5 mm/s, 0.05 mm/s and 0.001 mm/s, as the indentation rate $\dot{\delta}$.

Figure 6:
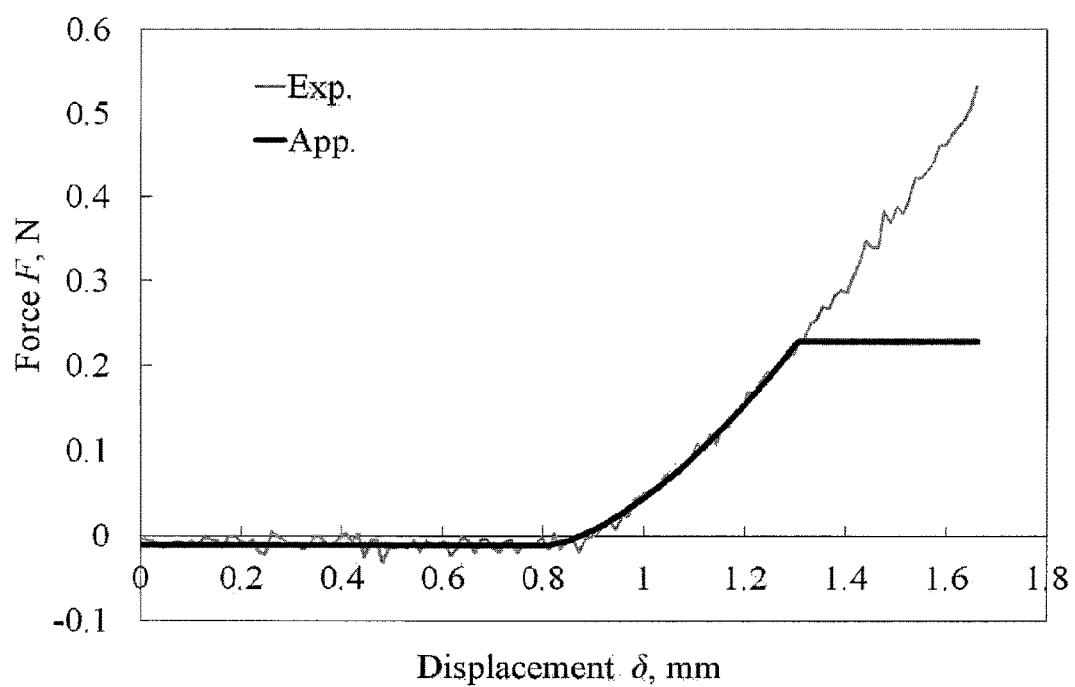
FIG. 6 shows one example of outputs from an indentation test device in a first example.

FIG. 6 shows one example of the output from the indentation test device in the first example. FIG. 6 shows the relation between the loads F and the indentation amounts δ when the indentation rate $\dot{\delta}$ relative to the sample LV 2 is 0.5 mm/s. The gray line "Exp." is the measured value output by the indentation test device.

The average resistivity D was calculated by Expression 24 using the indentation rates $\dot{\delta}$, the loads F and the indentation amounts δ output from the indentation test device. Here, the Poisson's ratio s ν [–] of the samples were all presumed to 0.45. The range of the indentation amounts δ used in identification was set from the indenter contact point to 0.5 mm in common. The amount of change $\Delta\varepsilon_I^-$ of the strain was set to 0.01 (1%). The solid line "App." in FIG. 6 is the calculation value based on Expression 24. The average resistivity D was identified by fitting the curved part according to the calculation values to the measured values.

The average resistivity D relative to each indentation rate $\dot{\delta}$ obtained according to the above is shown in Table 1. Note that what shown were the average values of the results obtained by performing the test for five times at the same indentation rate $\dot{\delta}$.

TABLE 1

| | AVERAGE RESISTIVITY D [k Pa] | | |
|---|---|---|---|
| SAMPLE | δ = 0.5 | δ = 0.05 | δ = 0.001 |
| LV 2 | 222.5 | 152.5 | 113.9 |
| LV 4 | 121.0 | 73.4 | 48.5 |
| LV 6 | 125.7 | 63.3 | 42.3 |
| LV 8 | 24.6 | 14.7 | 11.6 |

Furthermore, the period of time t in Expression 16 was calculated using the indentation rates $\dot{\delta}$, the loads F and the indentation amounts δ output from the indentation test device. The period of time t relative to each indentation rate $\dot{\delta}$ obtained according to the above is shown in Table 2.

TABLE 2

| INDENTATION RATE $\dot{\delta}$ (mm/s) | 0.5 | 0.05 | 0.001 |
|---|---|---|---|
| TIME t (s) | 0.0414 | 0.414 | 20.7 |

For each sample, the viscosity compliance C and the vertical moduluses of elasticity $E^e$ and $E^{ve}$, which minimize the function f of Expression 29, were specified using three value sets of the periods of time t and the average resistivity D shown in Table 1 and Table 2.

Figure 7:
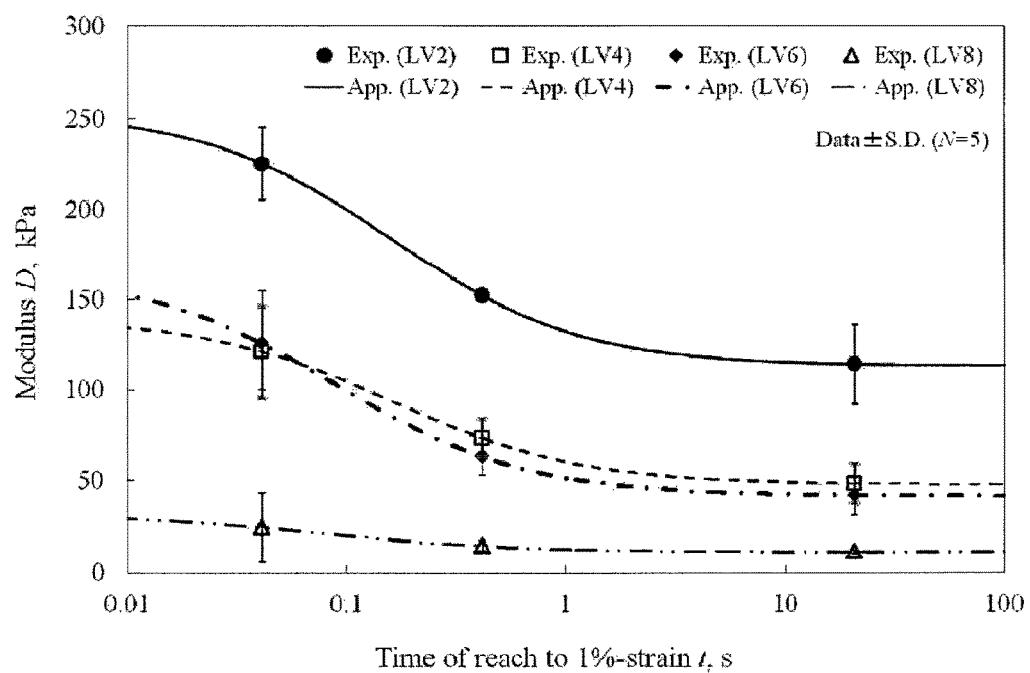
FIG. 7 shows values of periods of time t and average resistivity D calculated from a result of the test and calculation values in the first example.

FIG. 7 shows, in the first example, the periods of time t and the average resistivity D calculated from the measured values in the test, and shows the calculation values using the viscosity compliance C and the vertical moduluses of elasticity $E^e$ and $E^{ve}$ specified by the least-squares method in Expression 10. The values calculated from the test result are shown as "Exp.", and the calculation values according to the least-squares method are shown as "App.".

The viscosity coefficient μ was calculated using Expression 23 from the specified viscosity compliance C. Furthermore, the short-term vertical modulus of elasticity $D_0$ and the long-term vertical modulus of elasticity $D_\infty$ were calculated using Expression 17 and Expression 18 from the specified vertical moduluses of elasticity $E^e$ and $E^{ve}$.

Figure 8:
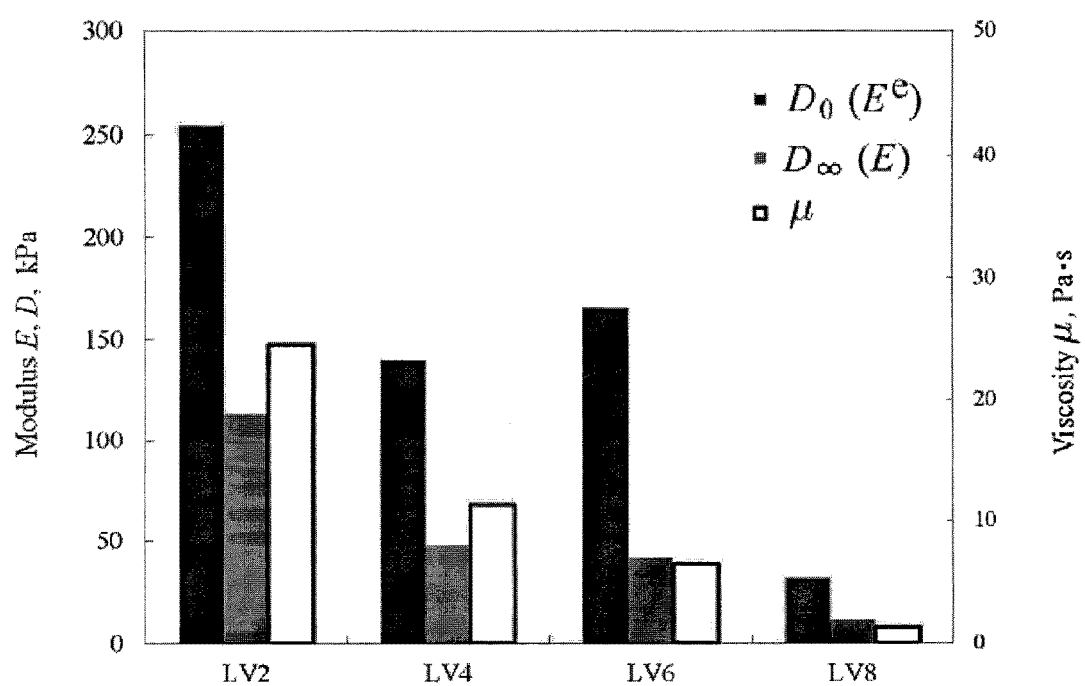
FIG. 8 shows values of viscosity coefficient μ, short-term vertical modulus of elasticity $D_0$ and long-term vertical modulus of elasticity $D_\infty$ for each sample in the first example.

FIG. 8 shows the viscosity coefficient μ, the short-term vertical modulus of elasticity $D_0$ and the long-term vertical modulus of elasticity $D_\infty$ for each sample in the first example. As described above, for each sample, the viscosity coefficient μ excluding the effects caused by the elasticity, and the long-term vertical modulus of elasticity $D_\infty$ corresponding to Young's modulus excluding the effects caused by the viscosity were calculated.

According to FIG. 8, since the viscosity coefficient μ and the short-term vertical modulus of elasticity $D_0$ of the sample LV2 are greater values than those of the other samples, it can be understood that the dependence of the sample LV2 on the strain rate $\dot{\varepsilon}$ is higher. Although the values of the long-term vertical moduluses of elasticity $D_\infty$ of LV4 and LV6 are close from each other, since LV4 has greater durometer hardness, according to a comparison of the viscosity coefficient μ and the short-term vertical modulus of elasticity $D_0$, it is considered that the viscosity coefficient μ also affects on the hardness. Therefore, it is found that not only Young's modulus E but also the viscosity coefficient μ should be taken into consideration for evaluation of the deformation property of the viscoelastic body. Furthermore, since there is an about ten-times difference in the values of the long-term vertical moduluses of elasticity $D_\infty$ between LV2 and LV8, it is found that the value of LV2 is about ten times of the value of LV8 when compared by Young's modulus E.

Figure 9:
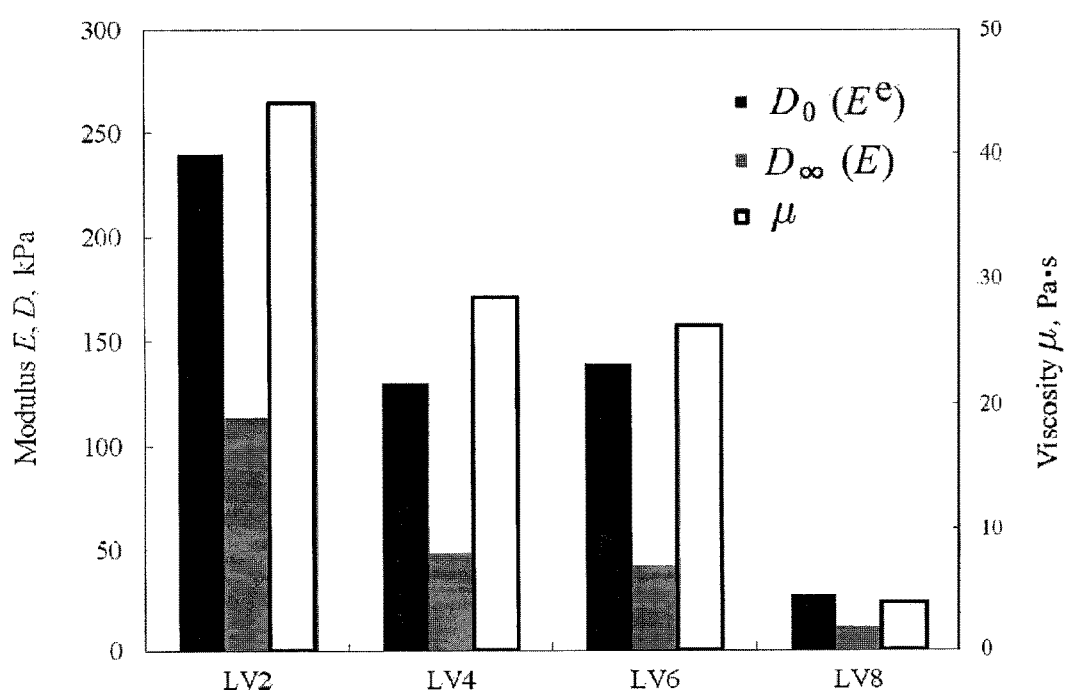
FIG. 9 shows values of viscosity coefficient μ, short-term vertical modulus of elasticity $D_0$ and long-term vertical modulus of elasticity $D_\infty$ for each sample in a first comparative example.

FIG. 9 shows the viscosity coefficients μ, the short-term vertical moduluses of elasticity $D_0$ and the long-term vertical moduluses of elasticity $D_\infty$ relative to each sample using the first comparative example. As shown in FIG. 9, corresponding to that the average resistivity D in Expression 27 is an exponential function for the periods of time t, as a result strongly depending on the period of time t, the value of the viscosity coefficient μ was calculated, which was about twice of the value in FIG. 8.

SECOND EXAMPLE

As a second example, for a β gel being a viscoelastic body, the viscosity coefficient μ was calculated similar to the first example based on the above-described embodiment. The indentation test device and the diameter φ of the ball indenter are the same as those in the first example.

The above-described β gel used in the test is primarily made of silicon as a raw material, and is a rectangular body with a width of 50 mm, a depth of 50 mm and a height of 20 mm. The β gel has very similar property to the property that an α gel has.

For the β gel, measured were the load F and the indentation amount 6 corresponding to the load F when indenting the ball indenter in a central part of the β gel at a constant indentation rate $\dot{\delta}$. The test was performed at three rates: 0.5 mm/s, 0.125 mm/s, and 0.01 mm/s, as the indentation rates $\dot{\delta}$.

The deformation resistivity D was calculated by Expression 24 using the indentation rates $\dot{\delta}$, the loads F and the indentation amounts δ output from the indentation test device. Here, the Poisson's ratio ν [-] of the samples were presumed to 0.45 which was the same as that of the first example. A range of the indentation amounts δ used in the identification was set from the indenter contact point to 0.5 mm, which was in common with the first example. The amount of change $\Delta\varepsilon_I^-$ of the strain was also set to 0.01 (=1%), which was the same as that of the first example. In a similar way to the first example, the relation between the load F and the indentation amount δ at each indentation rate $\dot{\delta}$ were graphed, and the deformation resistivity D was identified by fitting the curved part according to the calculation values based on Expression 24 to the measured values. It should be noted that, similar to the first example, an average was also calculated by performing the test at each indentation rate $\dot{\delta}$ for five times in the second example.

Furthermore, the period of time t in Expression 16 was calculated using the indentation rates $\dot{\delta}$, the loads F and the indentation amounts δ output from the indentation test device. The viscosity compliance C and the vertical moduluses of elasticity $E^e$ and $E^{ve}$, which minimize a function f of Expression 29, were specified using three value sets of the periods of time t and the deformation resistivity D corresponding to each indentation rate $\dot{\delta}$.

Figure 10:
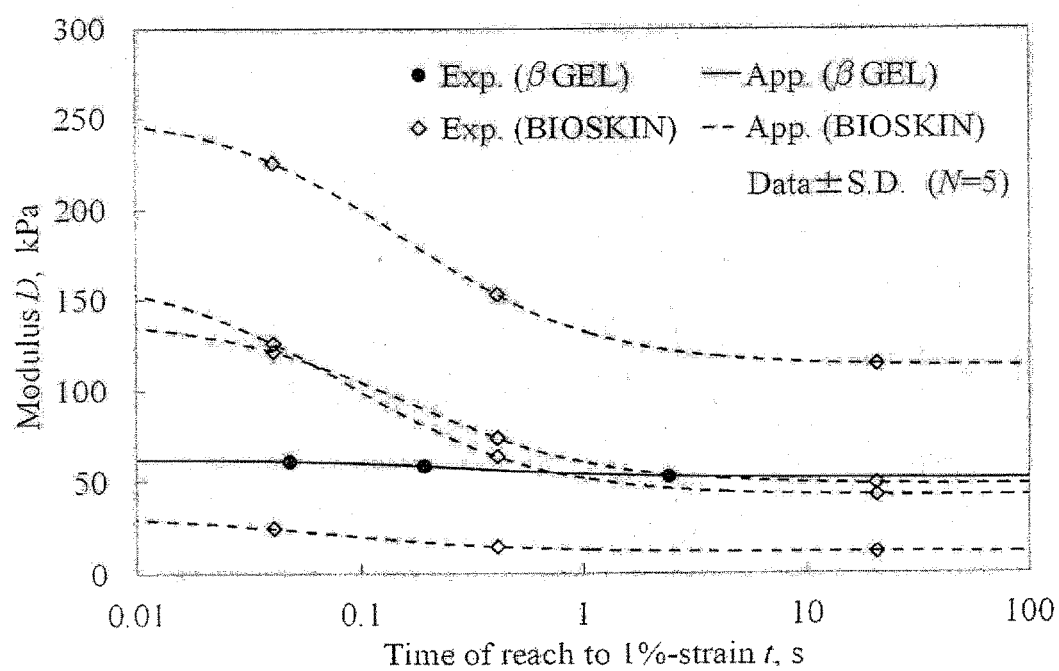
FIG. 10 shows values of periods of time t and average resistivity D calculated from a result of the test and calculation values in a second example.

FIG. 10 shows, in the second example, the periods of time t and the deformation resistivity D calculated from the measured values of the test, and the calculation values using the viscosity compliance C and the vertical moduluses of elasticity $E^e$ and $E^{ve}$ specified by the least-squares method in Expression 10. The values calculated from the result of the test are shown as "Exp." and the calculation values according to the least-squares method are shown as "App.". It should be noted that the data of the first example is also shown in FIG. 10 for comparison.

The viscosity coefficient μ was calculated from the specified viscosity compliance C using Expression 23. Furthermore, the short-term vertical modulus of elasticity $D_0$ and the long-term vertical modulus of elasticity $D_\infty$ were calculated from the specified vertical moduluses of elasticity $E^e$ and $E^{ve}$ using Expression 17 and Expression 18.

Figure 11:
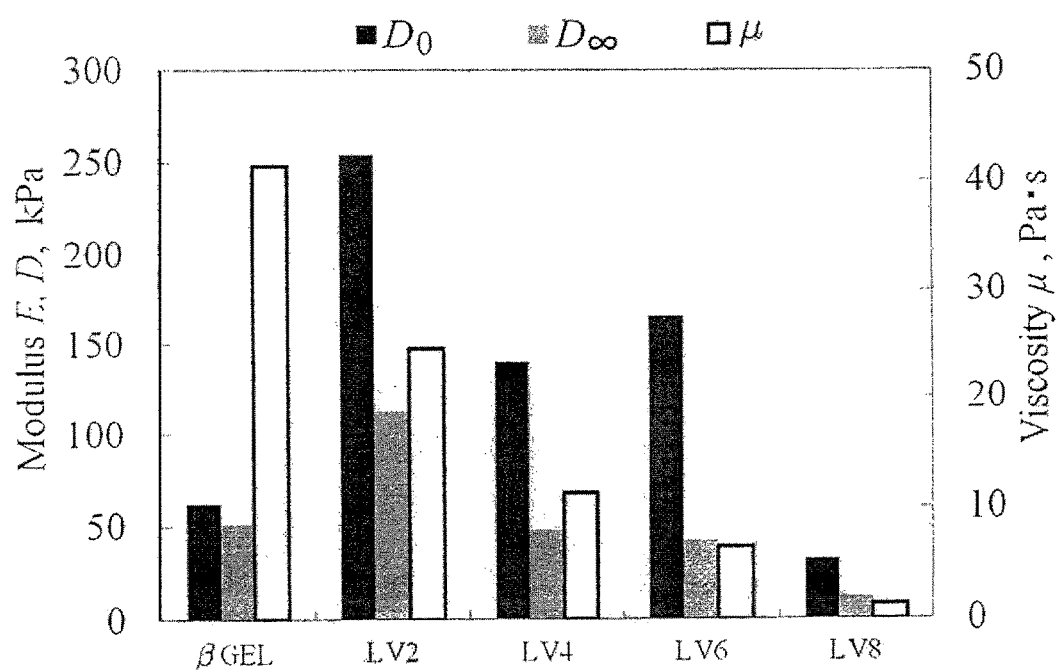
FIG. 11 shows values of viscosity coefficient μ, short-term vertical modulus of elasticity $D_0$ and long-term vertical modulus of elasticity $D_\infty$ for a β gel in the second example.

FIG. 11 shows the viscosity coefficient μ, the short-term vertical modulus of elasticity $D_0$ and the long-term vertical modulus of elasticity $D_\infty$ for the β gel in the second example. The data of the first example is also shown in FIG. 11 for comparison. In this way, for the β gel, the viscosity coefficient μ excluding the effects caused by the elasticity, and the long-term vertical modulus of elasticity $D_\infty$ corresponding to Young's modulus excluding the effects caused by the viscosity were calculated.

According to FIG. 11, the short-term vertical modulus of elasticity $D_0$ and the long-term vertical modulus of elasticity $D_\infty$ for the β gel are respectively 62.2 k Pa and 51.2 k Pa, and the difference between them is small and both are small. Accordingly, it can be considered that the β gel has a low dependency on the strain rate $\dot{\varepsilon}$. Furthermore, the viscosity coefficient of the β gel is about 250 Pa·s and is very large comparing with each sample in the first example. Accordingly, it can be understood that the β gel has an impact absorbing property. As described above, since the β gel is soft even in a region where the strain rate $\dot{\varepsilon}$ is high and has a very high viscosity only, it is confirmed that the β gel is almost dominant as a substance in the elastic part and is a solid that only has the viscosity property.

As described above, according to the present embodiment, it can identify the viscosity coefficient μ more conveniently and accurately. Particularly, since Expression 10 analytically solving Expression 7 is used, it can identify the viscosity coefficient μ more accurately. Furthermore, Expression 10 is a fractional function where both the denominator and the numerator include a first-order term of the periods of time t. Accordingly, the actual calculation by the numerics is also easy and it can approximately offset the effects caused by the time on the calculation of the viscosity coefficient μ. Also, the value of viscosity coefficient μ can be identified under a more uniform condition by using Expression 16 in the period of time t when identifying the parameters in Expression 10. Furthermore, since it is sufficient that the number of the value sets of the periods of time t and the deformation resistivity D (including the average resistivity D) is about the number of the parameters, the time for the test decreases and the calculation time are also decreased.

It should be noted that in the viscosity coefficient calculation device 12 shown in FIG. 4, in a case where the resistivity acquiring part 124 can directly acquire the deformation resistivity D and the period of time t from the outside, the load acquiring part 120 and the resistivity calculation part 122 may not be necessary. Also, a part or all of the functions of the viscosity coefficient calculation device 12 may be embedded within the indentation test device 10.

In the indentation test device 10, although the ball indenter 112 was described as an example, the shape of the indenter is not limited to a ball shape.

As other examples, a cylindrical or cube shape and the like may be adopted.

As a material of the indenter, metal and/or resin material and the like may be adopted.

When using the ball indenter 112, it is preferable to set the diameter φ in a range of $1\times10^{-8}$ m to 1 m. If the thickness h of the sample 20 is greater than the diameter φ of the ball indenter 112, there is an advantage that an equivalent result as the solution by Hertz's theory can be obtained. If the thickness h of the sample 20 is less than the diameter φ of the ball indenter 112, there is an advantage that Young's modulus can be identified, which was difficult to be identified by Hertz's theory.

In a case where the ball indenter 112 is used, it is preferable to set the indentation rate $\dot{\delta}$ in a range of 1 nm/s to 10 m/s. If the indentation rate $\dot{\delta}$ of the ball indenter 112 is greater than 1 nm/s, there is an advantage that time for measuring does not increase. If the indentation rate $\dot{\delta}$ of the ball indenter 112 is less than 10 m/s, there is an advantage that the device can be operated safely.

As a method for reducing the adhesion between the ball indenter 112 and the contact surface of the sample 20, a method for coating talc powder on the contact surface of the sample, a method for coating oil on the contact surface of the sample and the like can be adopted. It should be noted that in a cases where the adhesion between the ball indenter 112 and the contact surface of the sample 20 is low, these processes can be omitted.

As the sample 20 for measuring the viscosity coefficient $\mu$ and the like in the present embodiment, a polymer material including polyurethane, silicon rubber, polyolefin rubber, natural rubber and soft vinyl, a biotissue including skins or muscles, food including jelly or gelatin, and the like may be exemplified. Particularly, if the indentation test by the ball indenter can be executed without cutting the sample 20, it is possible to identify nonlinear physical property values in the viscoelastic behaviors of human soft tissue according to a less invasive in situ measurement.

It is preferable to set Young's modulus E of the sample 20 in a range of 10 Pa to 100 M Pa. If Young's modulus E is greater than 10 Pa, there is an advantage that the sample 20 does not collapse or break due to the indentation. If Young's modulus E is less than 100 M Pa, there is an advantage that a relatively soft indenter can also be used.

It is preferable to set the viscosity coefficient $\mu$ of the sample 20 in a range of 10 Pa·s to 100 M Pa·s. If the viscosity coefficient $\mu$ is less than 100 M Pa·s, there is an advantage that the viscosity behavior can be identified. If the viscosity coefficient $\mu$ is greater than 10 Pa·s, there is an advantage that the measurement can be performed without the collapse of the sample.

Although the three-element solid model being one example of a model of the sample 20 having viscoelasticity was used in the present embodiment, other samples such as, for example, the Maxwell model or the Voigt model being two-element solid models may be used in other models. Also, instead of the indentation test using the indentation test device, a tensile test using a tensile testing device may be used. In this case, instead of the indentation rate $\dot{\delta}$, the indentation amount $\delta$ and the indentation load F in the above-described embodiment, a pulling rate, a pulling amount and a pulling load may be used.

Figure 12:
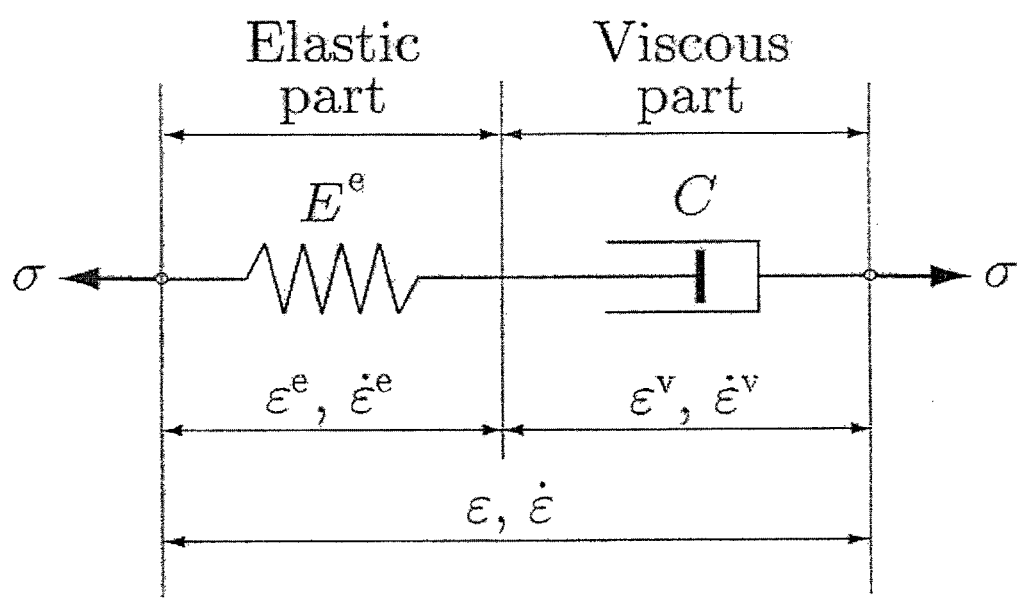
FIG. 12 shows a Maxwell model being one example of a model of a sample having viscoelasticity.

Here, a method will be simply described, which is for analytically obtaining the deformation resistivity D as a fractional function for periods of time t when using the Maxwell model being the above-described two-element solid model in the present embodiment. FIG. 12 shows the Maxwell model being one example of a model of a sample having viscoelasticity.

With respect of the vertical modulus of elasticity $E^e$ of the elastic part and the viscosity compliance C of the dash pot element being the viscosity part, the relation of the following Expression 30 is satisfied.

$$\dot{\varepsilon} = \frac{\dot{\sigma}}{E^e} + C\sigma \quad \text{EXPRESSION 30}$$

The following Expression 31 is obtained by substituting the deformation resistivity D into the above-described Expression 30 and simplifying the expression. The following Expression 31 is an expression representing the deformation resistivity D as a fractional function for the periods of time t when using the Maxwell model being the two-element solid model.

$$D(t) = \frac{E^e}{1 + CE^e t} \quad \text{EXPRESSION 31}$$

According to the above-described expression 31, as long as the value sets of the periods of time t and the deformation resistivity D at that time are given, the viscosity compliance C and the vertical modulus of elasticity $E^e$ as the parameters can be identified. Furthermore, similar to the approach using the three-element solid model, the value of the viscosity coefficient $\mu$ can be identified by identifying the value of the viscosity compliance C. In this way, in the present embodiment, as one example of the model of the sample 20 having viscoelasticity, the Maxwell model being the two-element solid model can be used. For example, for the sample 20 being a viscoelastic body approximately like a liquid, a two-element solid model suitable for liquids may be used.

Here, as an application example of the present embodiment, a method for calculating the viscosity coefficient on a surface of circular tube will be described. It will be described using an artery for one example as a circular tube. The method for calculating the viscosity coefficient of the artery described comprises: first, measuring a relative displacement of diameter of the artery varying due to the pulsation of the artery, measuring a blood pressure in the artery varying due to the pulsation of the artery, calculating representative values of an absolute displacement of the diameter of the artery and the deformation resistivity of the artery from the measured relative displacement and the blood pressure, and further calculating variation values of the deformation resistivity from the calculated absolute displacement.

For a material having a cylindrical shape such as a blood vessel, by using a thick cylinder deformation model or a thin cylinder deformation model, it is theoretically possible to obtain objective mechanical information such as the modulus of elasticity (Young's modulus) and the like from the relation between the pressures applied on a cylinder and the displacement amount (displacement). The deformation of the thick cylinder shell where the pressure P is applied from inside with two ends fixed can be represented by the following Expression 32.

$$u = \frac{1 - v^2}{E} \frac{\phi_1}{(\phi_1/\phi_i)^2 - 1} P \quad \text{EXPRESSION 32}$$

Here, u, E, v, $\phi_1$, and $\phi_i$ respectively indicate an absolute displacement of a radius, Young's modulus of the material of the cylinder, Poisson's ratio, an outer diameter of the cylinder shell and an inner diameter. It should be noted that the absolute displacement u of the radius is a value measured from an axis of the center of the cylinder being the reference toward outside in the radial direction, and is represented by a metric unit of length of meters.

Although the displacement u represented by the above-described Expression 32 changes proportionally only with the increases and decreases of the pressure P when Young's modulus E is a fixed number, an evaluation is necessary, which takes into consideration the deformation resistance influence caused by the viscosity effect on the blood vessel being biological soft tissues. For taking this influence into consideration, the deformation behavior of the blood vessel is evaluated by the following Expression 33 using the deformation resistivity D here, instead of Young's modulus E. It is possible to measure the relative displacement $\Delta u$ of the blood vessel deformation accompanying the variation of the blood pressure P, and it can evaluate the deformation behavior of the blood vessel by calculating the absolute displacement u of the blood vessel on the basis of this varying relative displacement $\Delta u$.

$$D = (1 - v^2) \frac{\phi_1}{(\phi_1/\phi_i)^2 - 1} \frac{P}{u} \quad \text{EXPRESSION 33}$$

In order to calculate the absolute displacement u from the relative displacement $\Delta u$, it is considered to measure the varying displacement $\Delta u$ as a relative value on the basis of an absolute value $u_0$ of the minimum displacement of the blood vessel deformation. At this time, by taking into consideration the measurement of the relative displacement $\Delta u$ from this minimum absolute displacement $u_0$, the absolute displacement u of the blood vessel deformation accompanying the variation of the blood pressure P can be represented by the following Expression 34 as a function for the periods of time t.

$$u(t) = \Delta u(t) + u_0 \quad \text{EXPRESSION 34}$$

By using the absolute displacement u (t) in the above-described expression 34, the deformation resistivity D (t) can be represented by the following Expression 35 while also using the varying blood pressure P (t) as the function for the periods of time t.

$$D(t) = (1 - v^2) \frac{\phi_1}{(\phi_1/\phi_i)^2 - 1} \frac{P(t)}{\Delta u(t) + u_0} \quad \text{EXPRESSION 35}$$

Here, by further taking into consideration a fixed number $D^-$ being a representative value of the varying deformation resistivity D (t), a function f ($D^-$, $u_0$) is newly defined, which is shown in the following Expression 36 having the representative deformation resistivity $D^-$ and the reference absolute displacement $u_0$ as variables.

$$f(\overline{D}, u_0) = \quad \text{EXPRESSION 36}$$
$$\sum_t \left\{ (1 - v^2) \frac{\phi_1}{(\phi_1/\phi_i)^2 - 1} P(t) - \overline{D}(\Delta u(t) + u_0) \right\}^2$$

Next, the blood pressure P (t), the deformation of the artery and the flow rate of the artery are measured respectively by appropriate sensors and the like to obtain each measurement value.

By calculating the variables ($D^-$, $u_0$) which minimize the function f ($D^-$, $u_0$) shown in the above-described Expression 36 according to the least-squares method, the deformation resistivity $D^-$ and the reference absolute displacement $u_0$ are calculated from the values of the blood pressure P (t) and the relative displacement $\Delta u$ (t) varying as the function for the periods of time t.

Furthermore, by using the obtained reference displacement $u_0$ and the above-described Expression 35, the deformation resistivity D (t) varying as the function for the periods of time t can be calculated.

Then, by substituting the value sets of the periods of time t and the deformation resistivity D at that time calculated here into the previously mentioned Expression 10 described in the present embodiment, it can identify the viscosity compliance C and the vertical moduluses of elasticity $E^e$ and $E^{ve}$ as the parameters being used in the viscosity coefficient calculation method in the present embodiment. Furthermore, by substituting the value of the viscosity compliance C identified by the above-mentioned Expression 23 described in the present embodiment, the value of the viscosity coefficient $\mu$ can be identified.

As other application examples for the present embodiment, other calculation methods for viscosity coefficient on the surface of circular tube will be described. As a circular tube, an artery will be described being exemplified as one example. The viscosity coefficient calculation method for the artery describing here comprises: first measuring, by an indenter pressing the artery, a varying load generated by pulsation of the artery, measuring a varying blood pressure of the artery, calculating, from the measured load and the blood pressure, the representative values of the pressure and the deformation resistivity of the artery when the distance indented by the indenter equal to the outer diameter of the artery, and further calculating variation values of the deformation resistivity from the calculated pressures.

A case is considered where two parallel cylindrical rigid indenters contact with an elastic cylindrical sample crossing orthogonally so as to be sandwiched by the two parallel cylindrical rigid indenters. At this time, the following Expression 37 is obtained from Hertz's theory of elastic contact, if setting a load generated by the contact as F, an indentation amount as $\delta$, a diameter of an indenter as $\varphi_0$, a diameter of a sample as $\varphi_1$, a Young's modulus of the sample as E, a Poisson's ratio as $v$, a Hertz coefficient with respect to a proximity amount determined from a ratio of the diameters $\varphi_0$ and $\varphi_1$ as $\lambda$.

$$F = \frac{4}{3} \frac{E}{1 - v^2} \frac{1}{\lambda^{3/2}} \left( \frac{\phi_1 \phi_0}{\phi_1 + \phi_0} \right)^{1/2} \delta^{3/2} \quad \text{EXPRESSION 37}$$

Also, at this time, upon presuming that a contact surface S becomes an ellipse, a long-axial radius a and a uniaxial radius b are respectively represented in the following Expression 38.

$$a = \left(\frac{3}{2}\right)^{1/3} \alpha \left[ \frac{F}{(2/\phi_1 + 2/\phi_0)} \frac{1 - v^2}{E} \right]^{1/3} \quad \text{EXPRESSION 38}$$
$$b = \left(\frac{3}{2}\right)^{1/3} \beta \left[ \frac{F}{(2/\phi_1 + 2/\phi_0)} \frac{1 - v^2}{E} \right]^{1/3}$$

It should be noted that $\alpha$ and $\beta$ are Hertz coefficients with respect to the long and short radiuses of the contact ellipse. The contact surface S is represented in the following Expression 39 from the above-described Expression 37 and Expression 38. Also, each physical property value is represented as shown in the following expression 40.

$$S = \pi a' b' \left(\frac{F}{E}\right)^{2/3} = \pi a' b' A^{2/3} \delta \quad \text{EXPRESSION 39}$$

$$\begin{aligned} a' &= \left(\frac{3}{2}\right)^{1/3} \alpha \left[\frac{1-v^2}{2/\phi_1 + 2/\phi_0}\right]^{1/3} \\ b' &= \left(\frac{3}{2}\right)^{1/3} \beta \left[\frac{1-v^2}{2/\phi_1 + 2/\phi_0}\right]^{1/3} \\ A &= \frac{4}{3} \frac{1}{\lambda^{3/2}(1-v^2)} \left(\frac{\phi_1 \phi_0}{\phi_1 + \phi_0}\right)^{1/2} \end{aligned} \quad \text{EXPRESSION 40}$$

If setting an internal pressure applied to the sample as P, the contact and the load F generated by the internal pressure P becomes in a relation shown in the following Expression 41.

$$F = \pi a' b' A^{2/3} \delta P \quad \text{EXPRESSION 41}$$

However, it is difficult to measure the indentation amount $\delta$ in the artery during actual pulsation. Here, if setting the pressure when the distance indented by the indenter is equal to the diameter of the sample as $P_0$, the indentation amount in a state where the internal pressure is zero as $\delta_0$, the internal pressure in the period of time t as P (t) and the indentation amount under the P (t) as $\Delta\delta$, F (t) is obtained by the following Expression 42.

$$F(t) = \pi a' b' A^{2/3} (\Delta\delta(t) + \delta_0)(P(t) + P_0) \quad \text{EXPRESSION 42}$$

Here, a deformation of a thin cylinder shell where an internal pressure is applied is considered. Since the deformation resistance is generated by the viscosity on the deformation of the artery, for taking that influence into consideration, if using the deformation resistivity D instead of the modulus of elasticity, a displacement amount u (t) in the period of time t becomes the following Expression 43.

$$u(t) = \frac{1-v^2}{D} \frac{\phi_i^2}{2(\phi_1 - \phi_i)} P(t) \quad \text{EXPRESSION 43}$$

Note that a deformation amount in the radial direction is set as u and an inner diameter is set as $\phi_i$. If substituting the deformation amount u (t) accompanying the pressure changes, considered as the indentation amount $\Delta\delta$ (t) of the indenter, into the above-described Expression 42 further considering the relation between the pressure $P_0$ and the indentation amount $\delta_0$ from the expression (Expression 12), the following Expression 44 is obtained.

$$D(t) = \pi a' b' A^{2/3} \frac{(1-v^2)\phi_i^2}{2(\phi_1 - \phi_i)} \frac{(P(t) + P_0)^2}{F(t)} \quad \text{EXPRESSION 44}$$

Setting the fixed number $D^-$ as a representative value of the deformation resistivity D, a residual $f(D^-, P_0)$ in the following expression is defined.

$$f(\overline{D}, P_0) = \quad \text{EXPRESSION 45}$$
$$\sum_t \left\{ F(t) - \pi a' b' A^{2/3} \frac{1-v^2}{\overline{D}} \frac{\phi_i^2}{2(\phi_1 - \phi_i)} (P(t) + P_0)^2 \right\}^2$$

Next, the blood pressures P (t), the loads generated in the indenter sandwiching the artery and the flow rate in the artery are measured respectively by appropriate sensors and the like to obtain each measurement value.

$P_0$ is calculated from the load F (t) and the pressure P (t) by calculating $(D^-, P_0)$, which minimize $f(D^-, P_0)$ in the above-described Expression 45, by the least-squares method. The deformation resistivity D (t) is calculated by substituting the obtained $P_0$ into the above-described Expression 44.

Then, by substituting the value sets of the calculated period of time e t and the deformation resistivity D at that time into the previously mentioned Expression 10 described in the present embodiment, the viscosity compliance C and the vertical moduluses of elasticity $E^e$ and $E^{ve}$ can be identified, which are as the parameters used in the viscosity coefficient calculation method in the present embodiment. Furthermore, by substituting the value of the viscosity compliance C identified in the previously mentioned Expression 23 described in the present embodiment, the value of the viscosity coefficient μ can be identified.

As described above, as application examples of the present embodiment, two calculation methods for viscosity coefficient on the surface of circular tube were described. Each calculation method can be used appropriately depending on whether the detected parameters are the varying relative displacements of the pressure wall or the varying loads generated by the pulsation pf the pressure wall.

As described above, according to the present embodiment, even if the data observable by the shape of the sample 20 is different, the viscosity coefficient can be identified using the physical quantities of the viscoelasticity model calculated from the experimental data utilizing a geometric model of the shape.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an device, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

DESCRIPTION OF REFERENCE NUMERALS

10 . . . indentation test device, 12 . . . viscosity coefficient calculation device, 20 . . . sample, 100 . . . base, 102 . . . frame, 104 . . . head, 106 . . . actuator, 108 . . . load cell, 110 . . . load shaft, 112 . . . ball indenter, 114 . . . stage, 116 . . . control part, 120 . . . load acquiring part, 122 . . . resistivity calculation part, 124 . . . resistivity acquiring part, 126 . . . output part, 128 . . . viscosity calculation part, 130 . . . storage part

What is claimed is:

1. A viscosity coefficient calculation device, comprising:
a resistivity acquiring pert that acquires, when a load is applied to a sample, a value of deformation resistivity corresponding to an apparent modulus of elasticity when modulus of elasticity considered to be in accordance with Hook's law for each plurality of periods of time until a specific strain is generated; and
an output part that outputs a value of viscosity coefficient of the sample from the value of the deformation resistivity for the each plurality of periods of time acquired by the resistivity acquiring part using a relational expression that associates the deformation resistivity with a viscosity coefficient, the relational expression being a fractional function for periods of time, the relational expression analytically obtained by substituting the deformation resistivity to a first order differential equation for a stress and a strain obtained from a configuration expression of a viscoelasticity model.

2. The viscosity coefficient calculation device according to claim 1, wherein
the viscoelasticity model is a three-element solid model.

3. The viscosity coefficient calculation device according to claim 1, further comprising:
a load acquiring part that acquires, respectively corresponding to a plurality of rates at which loads are applied to the sample, a plurality of the loads and a plurality of one of indentation amounts and tensile amounts of the sample relative to the loads; and
a resistivity calculation part that calculates a value of the deformation resistivity for the each plurality of periods of time from the one of the indentation amounts and the tensile and the loads amounts acquired by the load acquiring part, and outputs the value to the resistivity acquiring part.

4. The viscosity coefficient calculation device according to claim 1, wherein
the output part has:
a storage part that stores the relational expression; and
a viscosity calculation part that calculates a value of viscosity coefficient of the sample by acquiring the value of the deformation resistivity for the each plurality of periods of time from the resistivity acquiring part and referring to the relational expression stored- in the storage part.

5. An indentation test device, comprising:
an indentation part that indents an indenter into a sample;
a load acquiring part that acquires, when the indenter is indented by the indentation part at rates different from each other, a plurality of loads of the indenter and indentation amounts of the sample relative to the loads corresponding to a plurality of the rates;
a resistivity calculation part that calculates from the plurality of the loads and the indentation amounts acquired by the load acquiring part a value of deformation resistivity corresponding to an apparent modulus of elasticity when modulus of elasticity considered to be in accordance with Hook's law for each plurality of periods of time by an expression based on Hertz's theory of elastic contact; and
an output part that outputs a value of viscosity coefficient of the sample from the value of the deformation resistivity for the each plurality of periods of time calculated by the resistivity calculation part using a relational expression associating the deformation resistivity with the viscosity coefficient, the relational expression being a fractional function for periods of time, the relational expression analytically obtained by substituting the deformation resistivity into a first order differential equation for a stress and a strain obtained from a configuration expression of a viscoelasticity model.

6. A tensile testing device, comprising:
a pulling part that pulls a sample;
a load acquiring part that acquires, when the sample is pulled by the pulling part at a plurality of rates different from each other, a plurality of tensile loads and tensile amounts of the sample relative to the loads corresponding to the plurality of the rates;
a resistivity calculation part that calculates a value of deformation resistivity corresponding to an apparent modulus of elasticity when modulus of elasticity considered to be in accordance with Hook's law for each plurality of periods of time from the plurality of the loads and the tensile amounts acquired by the load acquiring part based on Hertz's theory of elastic contact; and
an output part that outputs a value of viscosity coefficient of the sample from the value of the deformation resistivity for the each plurality of periods of time calculated by the resistivity calculation part using a relational expression associating the deformation resistivity with the viscosity coefficient, the relational expression being a fractional function for periods of time, the relational expression analytically obtained by substituting the deformation resistivity into a first order differential equation for a stress and a strain obtained from a configuration expression of a viscoelasticity model.

7. A viscosity coefficient calculation method comprising:
acquiring, when a load is applied to a sample, a value of deformation resistivity corresponding to a modulus of elasticity when modulus of elasticity considered to he in accordance with Hook's law for each plurality of periods of time until a specific strain is generated; and
outputting a value of viscosity coefficient of the sample from the acquired value of the deformation resistivity for the each plurality of periods of time using a relational expression associating the deformation resistivity with the viscosity coefficient, the relational expression being a fractional function for periods of time, the relational expression analytically obtained by substituting the deformation resistivity to a first order differential equation for a stress and a strain obtained from a configuration expression of a viscoelasticity model.

8. A non-transitory computer readable medium having a program embodied therewith, the program executable by a computer to cause the computer to perform operations comprising:
acquiring, for each plurality of periods of time until a specific strain is generated when a load is applied to a sample, a value of deformation resistivity corresponding to an apparent modulus of elasticity when modulus of elasticity considered to be in accordance with Hook's law; and
outputting a value of viscosity coefficient of the sample from the acquired value of the deformation resistivity for the each plurality of periods of time using a relational expression associating the deformation resistivity with the viscosity coefficient, the relational expression being a fractional function for periods of time, the relational expression analytically obtained by substituting the deformation resistivity into a first order differential equation For a stress and a strain obtained from a configuration expression of a viscoelasticity model.

9. The viscosity coefficient calculation device according to claim 1, wherein the relational expression that associates the deformation resistivity with a viscosity coefficient is $$D(t) = \frac{CE^e E^{ve} t + E^e}{C(E^e + E^{ve})t + 1}$$

where D(t) is the deformation resistivity, C is the viscosity compliance, and $E^e$ and $E^{ve}$ are the vertical moduluses of elasticity, and the viscosity coefficient, μ, inversely relates to the viscosity compliance of the sample.

* * * * *